United States Patent
Chiba et al.

(10) Patent No.: US 11,465,125 B2
(45) Date of Patent: Oct. 11, 2022

(54) WATER-ABSORBING RESIN

(71) Applicant: SUMITOMO SEIKA CHEMICALS CO., LTD., Hyogo (JP)

(72) Inventors: Mikito Chiba, Himeji (JP); Yuichi Onoda, Himeji (JP)

(73) Assignee: SUMITOMO SEIKA CHEMICALS CO., LTD., Hyogo (JP)

(*) Notice: Subject to any disclaimer, the term of this patent is extended or adjusted under 35 U.S.C. 154(b) by 292 days.

(21) Appl. No.: 16/490,037

(22) PCT Filed: Mar. 2, 2018

(86) PCT No.: PCT/JP2018/007961
§ 371 (c)(1),
(2) Date: Aug. 29, 2019

(87) PCT Pub. No.: WO2018/159802
PCT Pub. Date: Sep. 7, 2018

(65) Prior Publication Data
US 2020/0009528 A1 Jan. 9, 2020

(30) Foreign Application Priority Data
Mar. 2, 2017 (JP) .............................. JP2017-038981

(51) Int. Cl.
*B01J 20/26* (2006.01)
*B01J 20/28* (2006.01)
*C08F 20/06* (2006.01)

(52) U.S. Cl.
CPC ....... *B01J 20/261* (2013.01); *B01J 20/28019* (2013.01); *B01J 20/28042* (2013.01); *C08F 20/06* (2013.01)

(58) Field of Classification Search
CPC .... B01J 20/26; B01J 20/261; B01J 20/28019; B01J 20/28042; C08F 20/06
USPC ....................................................... 502/402
See application file for complete search history.

(56) References Cited

U.S. PATENT DOCUMENTS

| | | | |
|---|---|---|---|
| 5,180,798 | A | 1/1993 | Nakamura et al. |
| 2003/0181115 | A1 | 9/2003 | Nagasuna et al. |
| 2011/0059329 | A1 | 3/2011 | Dobrawa et al. |
| 2011/0313113 | A1 | 12/2011 | Sakamoto et al. |
| 2013/0130017 | A1 | 5/2013 | Takatori et al. |
| 2015/0011388 | A1 | 1/2015 | Matsumoto et al. |
| 2016/0367717 | A1 | 12/2016 | Hinayama et al. |
| 2017/0107313 | A1 | 4/2017 | Murakami et al. |
| 2017/0203279 | A1 | 7/2017 | Murakami et al. |
| 2017/0218096 | A1† | 8/2017 | Yabuguchi |
| 2018/0001300 | A1 | 1/2018 | Nakatsuru et al. |
| 2020/0001270 | A1 | 1/2020 | Chiba et al. |
| 2020/0002445 | A1 | 1/2020 | Chiba et al. |

FOREIGN PATENT DOCUMENTS

| | | |
|---|---|---|
| EP | 1364985 A1 | 11/2003 |
| EP | 1364992 A1 | 11/2003 |
| EP | 2 998 325 A1 | 3/2016 |
| EP | 2993191 A1 † | 3/2016 |
| JP | H03-227301 A | 10/1991 |
| JP | 2003-290290 A | 10/2003 |
| JP | 2007-154350 A | 6/2007 |
| JP | 2013-123515 A | 6/2013 |
| JP | 2014-098172 A | 5/2014 |
| JP | 2015-083693 | 4/2015 |
| KR | 10-2016-0017649 A | 2/2016 |
| WO | WO 2016/006132 A1 | 1/2016 |
| WO | WO 2016/111223 A1 | 7/2016 |

OTHER PUBLICATIONS

International Search Report for International Application No. PCT/JP2018/007961, dated Jun. 12, 2018 (in 1 page).
Supplementary European Search Report, European Patent Application No. 18 76 1807.9 dated Oct. 30, 2020.
Third Party Submission filed toward the counterpart European Patent Appln. No. 18761807.9 (Notification Date: Mar. 30, 2022) (6 pages).
Shimadzu Corporation, "Observations of Superabsorbent Polymers Using the inspeXio SMX-100CT Microfocus X-Ray CT System", 2013 (2 pages).
Boards of Appeal of the European Patent Office Data sheet for the Dec. 15, 2003 Decision of Appeal, in European Appeal No. EP0532002 (EP Patent Application No. 92115510.7) (23 pages).
Buchholz, Fredric L. and Graham, Andrew T., "Modern Superabsorbent Polymer Technology", 1998, Copyright by John Wiley & Sons, Inc., New York, 1998.
Korean Office Action in Korean Patent Application No. 10-2019-7025053 dated Jul. 25, 2022.

† cited by third party

*Primary Examiner* — Edward M Johnson
(74) *Attorney, Agent, or Firm* — Knobbe, Martens, Olson & Bear, LLP

(57) ABSTRACT

A water-absorbing resin that exhibits excellent absorption performance and a high permeation rate with respect to liquids to be absorbed, and that effectively reduces liquid leakages, even in an absorbent body using a large amount of the water-absorbing resin. The water-absorbing resin is formed from a polymer of a water-soluble ethylenically unsaturated monomer, and when a cross-sectional image of the water-absorbing resin obtained by X-ray computer tomography is observed, the percent area of cavity portions in the cross-sectional image is 2-10%. The liquid flow rate index when a physiological saline liquid column flow rate test is performed on the water-absorbent resin having a particle diameter of 250 to 500 μm at 37° C. is 5-20.

4 Claims, 1 Drawing Sheet

WATER-ABSORBING RESIN

TECHNICAL FIELD

The present invention relates to a water-absorbent resin and an absorbent article; more particularly, the present invention relates to a water-absorbent resin that constitutes an absorbent material suitably used for hygienic materials such as disposable diapers, sanitary napkins, and incontinence pads, and to an absorbent article comprising the water-absorbent resin.

BACKGROUND ART

In recent years, water-absorbent resins have been widely used in the field of hygienic materials such as disposable diapers, sanitary napkins, and incontinence pads.

As such water-absorbent resins, cross-linked products of partially neutralized acrylic acid polymers have been proposed as preferable water-absorbent resins, because they have many advantages, for example, as follows: they have good water-absorption capacity, and acrylic acid used as a raw material is readily industrially available, and thus, they can be produced at low cost with uniform quality additionally, they are resistant to decomposition or degradation for example, Patent Document 1).

An absorbent article such as a disposable diaper, a sanitary napkin, or an incontinence pad is composed of an absorbent material that absorbs and retains a body liquid such as urine or menses excreted from the body, the absorbent material being positioned mainly in a central portion, a liquid-permeable front sheet (top sheet) positioned on the side of the absorbent article that is brought into contact with the body, and a liquid-impermeable rear sheet (back sheet) positioned opposite to the side that is brought into contact with the body. The absorbent material is composed of hydrophilic fibers such as pulp and a water-absorbent resin.

Conventionally, there has been an increasing demand for thinner and lighter absorbent articles from the viewpoint of design, convenience in carrying, and efficiency in distribution. Furthermore, in recent years, from the viewpoint of environmental conservation, there has been a growing need for a so-called eco-friendly intention to effectively utilize resources, and minimize the use of natural materials that require a long time to grow, such as trees. Examples of common methods for reducing the thickness of such an absorbent article include a method in which the amount of a water-absorbent resin is increased while reducing the amount of hydrophilic fibers, such as crushed pulp from wood, that serve to fix the water-absorbent resin in the absorbent material. Moreover, extensive research has been conducted on absorbent laminates, water-absorbent sheets, and the like that are substantially free of hydrophilic fibers within the absorbent layer.

PRIOR ART DOCUMENT

Patent Document

Patent Document 1: Japanese Patent Laid-open Publication No. H3-227301

SUMMARY OF THE INVENTION

Problems to be Solved by the Invention

An absorbent material having a reduced proportion of hydrophilic fibers and an increased proportion of a water-absorbent resin is preferable for achieving a smaller thickness, from the viewpoint of reducing the bulky hydrophilic fibers, and retaining a liquid. However, in situations where a water-absorbent sheet including the water-absorbent resin is subjected to a load due to a deformation, a pressure, or the like, such as in a situation where an infant wearing a thinned absorbent article is sitting, the absorbent article may not sufficiently prevent liquid leakage. Furthermore, the absorbent article may not tolerate a plurality of discharges of urine, possibly causing discomfort to the wearer.

A large amount of water-absorbent resin is formed into the shape of a soft by the absorption of the liquid, and furthermore, when a load is applied to the gel, a so-called "gel blocking phenomenon" occurs, and thus the liquid diffusibility is significantly lowered, with the result that the permeation rate of the liquid by the absorbent material may be lowered. The "gel blocking phenomenon" refers to a phenomenon in which especially when the absorbent material where a large amount of water-absorbent resin is densely present absorbs the liquid, the water-absorbent resin present around a front layer absorbs the liquid to form a soft gel around the front layer and the gel becomes dense to prevent the permeation of the liquid into the absorbent material, with the result that the water-absorbent resin therewithin cannot efficiently absorb the liquid.

As a means for preventing those problems occurring when the hydrophilic fiber is reduced and a large amount of water-absorbent resin is used, for example, the following methods have so far been proposed: a method of using a hydrogel water-absorbent polymer having specific saline flow conductivity, performance under pressure and the like; and a method of using a water-absorbent resin obtained by heating and processing a specific surface crosslinking agent on a specific water-absorbent resin precursor. In these methods, however, the absorption performance of the absorbent material where a large amount of water-absorbent resin is used is not always satisfied, and there is a tendency that a to-be-absorbed liquid cannot be captured, and that thus the liquid disadvantageously leaks.

The present invention has a main object to provide a water-absorbent resin that exhibits excellent absorption performance and a high permeation rate with respect to liquids to be absorbed, and that effectively reduces liquid leakages, even in an absorbent material using a large amount of the water-absorbent resin.

Means for Solving the Problem

The inventors of the present invention conducted a diligent study to solve the aforementioned problem. As a result, the water-absorbent resin is formed from a polymer of a water-soluble ethylenically unsaturated monomer, and when a cross-sectional image of the water-absorbent resin obtained by X-ray computed tomography is observed, the ratio (cavity area ratio) as calculated by Equation (I) shown below of the area of cavity portions in the cross-sectional image is 2 to 10%, and the particle diameter is 250 to 500 µm. In this water-absorbent resin, the liquid flow rate index as calculated by Equation (II) shown below when a physiological saline liquid column flow rate test is performed on the water-absorbent resin having a particle diameter of 250 to 500 µm at 37° C. is 5 to 20. As a result, it has been found that the water-absorbent resin exhibits excellent absorption performance and a high permeation rate with respect to liquids to be absorbed, and that effectively reduces liquid leakages, even in an absorbent material using a large amount of the water-absorbent resin.

Cavity area ratio [%]={total cross-sectional area (B) of cavity portions of the water-absorbent resin/ (total cross-sectional area (A) of resin portions of the water-absorbent resin+total cross-sectional area (B) of cavity portions of the water-absorbent resin)}×100.  (I)

Liquid flow rate index={liquid flow rate (CPR2) during 10 second period between 50 seconds and 60 seconds after initiation of liquid flow/ liquid flow rate (CPR1) during 10 second period after initiation of liquid flow}×100.  (II)

The present invention has been accomplished as a result of further study based on these findings.

In summary, the present invention provides aspects of the invention comprising the following features:

Item 1. The water-absorbent resin is formed from a polymer of a water-soluble ethylenically unsaturated monomer, and when a cross-sectional image of the water-absorbent resin obtained by X-ray computed tomography is observed, the ratio (cavity area ratio) as calculated by Equation (I) shown below of the area of cavity portions in the cross-sectional image is 2 to 10%. In this water-absorbent resin, the liquid flow rate index as calculated by Equation (II) shown below when a physiological saline liquid column flow rate test is performed on the water-absorbent resin having a particle diameter of 250 to 500 μm at 37° C. is 5 to 20.

Cavity area ratio [%]={total cross-sectional area (B) of cavity portions of the water-absorbent resin/ (total cross-sectional area (A) of resin portions of the water-absorbent resin+total cross-sectional area (B) of cavity portions of the water-absorbent resin)}×100.  (I)

Liquid flow rate index={liquid flow rate (CPR2) during 10 second period between 50 seconds and 60 seconds after initiation of liquid flow/ liquid flow rate (CPR1) during 10 second period after initiation of liquid flow}×100.  (II)

Item 2. The water-absorbent resin according to item 1, wherein the water-absorbent resin has a physiological saline-retention capacity of 35 g/g or less.

Item 3. The water-absorbent resin according to item 1 or 2, wherein the water-absorbent resin has a substantially spherical shape or a shape in which particles having a substantially spherical shape are aggregated.

Item 4. The water-absorbent resin according to any one of items 1 to 3, which is used in an adsorbent material designed to have a proportion of the water-absorbent resin of 50% by mass or more in the adsorbent material.

Advantages of the Invention

The present invention can provide a water-absorbent resin that exhibits excellent absorption performance and a high permeation rate with respect to liquids to be absorbed, and that effectively reduces liquid leakages, even in an absorbent material using a large amount of the water-absorbent resin. Furthermore, in accordance with the present invention, there is provided an absorbent article using the water-absorbent resin.

EMBODIMENTS OF THE INVENTION

1. Water-Absorbent Resin

The water-absorbent resin is formed from a polymer of a water-soluble ethylenically unsaturated monomer, and when a cross-sectional image of the water-absorbent resin obtained by X-ray computed tomography is observed, the ratio (cavity area ratio) as calculated by Equation (I) shown below of the area of cavity portions in the cross-sectional image is 2 to 10%. In this water-absorbent resin, the liquid flow rate index as calculated by Equation (II) shown below when a physiological saline liquid column flow rate test is performed on the water-absorbent resin having a particle diameter of 250 to 500 μm at 37° C. is 5 to 20.

Cavity area ratio [%]={total cross-sectional area (B) of cavity portions of the water-absorbent resin/ (total cross-sectional area (A) of resin portions of the water-absorbent resin+total cross-sectional area (B) of cavity portions of the water-absorbent resin)}×100.  (I)

Liquid flow rate index={liquid flow rate (CPR2) during 10 second period between 50 seconds and 60 seconds after initiation of liquid flow/ liquid flow rate (CPR1) during 10 second period after initiation of liquid flow}×100.  (II)

The water-absorbent resin of the present invention having such a configuration exhibits excellent absorption performance and a high permeation rate with respect to liquids to be absorbed, and that effectively reduces liquid leakages, even in an absorbent material using a large amount of the water-absorbent resin. The water-absorbent resin of the present invention will be hereinafter described in detail.

Figure 2:
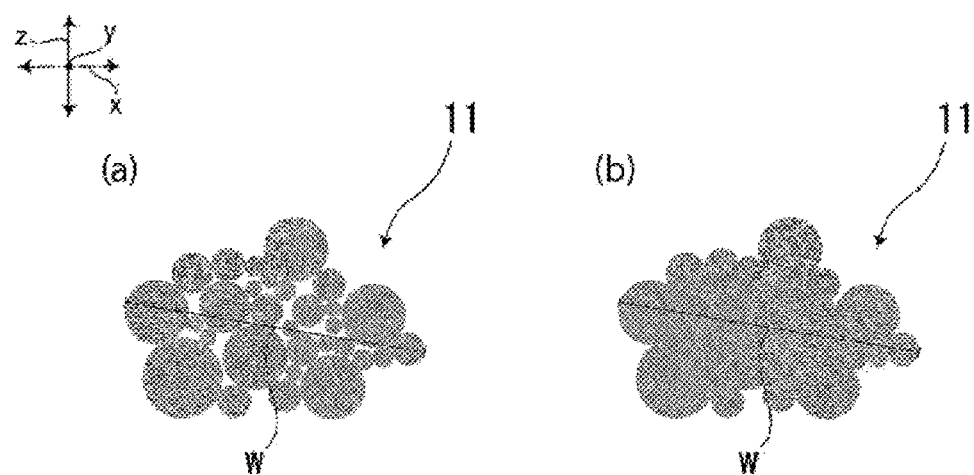
FIG. 2(a) is a schematic diagram of a cross-sectional image of a water-absorbent resin taken using X-ray computed tomography.
FIG. 2(b) is a schematic diagram prepared by filling the cavity portions of FIG. 2(a).

As used herein, the phrase "total cross-sectional area of resin portions in the water-absorbent resin" refers to the total cross-sectional area of portions where the water-absorbent resin is present (filled portions) in the cross-sectional image of the water-absorbent resin, as shown in the schematic diagram of FIG. 2(a), for example. The phrase "total cross-sectional area of cavity portions in the water-absorbent resin" refers to the total area of cavity portions in the water-absorbent resin (blank portions in the water-absorbent resin) in the cross-sectional image of the water-absorbent resin, as shown in the schematic diagram of FIG. 2(a), for example.

Examples of shapes of the water-absorbent resin of the present invention include a substantially spherical shape, a shape in which particles having a substantially spherical shape are aggregated, a crushed indefinite shape, a shape in which particles having a crushed indefinite shape are aggregated, and a flat shape. Through the use of reversed phase suspension polymerization or spray droplet polymerization, a water-absorbent resin having a substantially spherical single-particle shape, such as a spherical or elliptical shape, or a shape in which single particles having a substantially spherical shape are aggregated, can be produced. Through the use of aqueous solution polymerization, a water-absorbent resin having a crushed indefinite shape or a shape in which particles having a crushed indefinite shape are aggregated can be produced. From the viewpoint of controlling the cavity area ratio, preferred as the shape of the water-absorbent resin is a substantially spherical shape or a shape in which particles having a substantially spherical shape are aggregated.

When a cross-sectional image of the water-absorbent resin is observed using X-ray computed tomography, the water-absorbent resin has a ratio of the area of cavity portions (cavity area ratio) in the cross-sectional image of 2 to 10%, as calculated according to Equation (I) above. The cavity area ratio is preferably 2 to 9%, and more preferably 5 to 8%, from the viewpoint of achieving a water-absorbent resin that exhibits excellent absorption performance and a high permeation rate with respect to liquids to be absorbed, and that effectively reduces liquid leakages, even in an absorbent material using a large amount of the water-absorbent resin.

In the present invention, the cavity area ratio is measured as follows, using X-ray computed tomography.

<Measurement of Cavity Area Ratio Using X-ray Computed Tomography>

Particles of the water-absorbent resin are classified in advance with JIS standard sieves. Four particles are randomly selected from particles of the water-absorbent resin on a sieve with a mesh size of 180 μm that pass through a sieve with a mesh size of 600 μm, and these particles are used as resin samples. The resin samples are placed on a sample stage of an X-ray computer tomography apparatus, and cross-sectional image data are acquired using X-ray computer tomography. Next, for each of the resin samples, shapes at given angles or given horizontal and vertical cross sections are observed using image analysis software.

Figure 1:
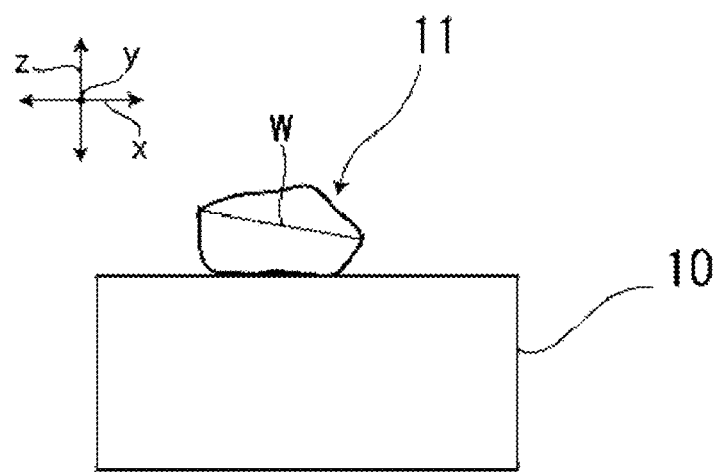
FIG. 1 is a schematic diagram for use in illustrating a method for measuring the cavity area ratio of a water-absorbent resin using X-ray computed tomography.

Here, from given cross sections in horizontal directions (x- and y-directions) and a vertical direction (z-direction) with respect to the mounting surface of the sample stage, a horizontal or vertical cross-sectional image having a maximum distance between given two points on the contour of each of the resin samples is selected. Specifically, as shown in the schematic diagram of FIG. 1, for each of the three directions, x-, y-, and z-directions, that are perpendicular to one another, cross-sectional images of a resin sample 11 on a sample stage 10 are acquired first. Subsequently, for each of these directions, one cross-sectional image having the longest particle length w (see FIGS. 1 and 2) of the resin sample (i.e., a cross-sectional image taken in a position where the particle length of the resin sample is the longest) is selected. Then, a cross-sectional image having the longest particle length w of the resin sample of these three cross-sectional images is selected.

Next, the cavity area ratio is calculated using this cross-sectional image. By means of general-purpose image processing software, the cross-sectional area of the resin sample (total cross-sectional area of resin portions (A) in the water-absorbent resin) (the area of the filled portions in the schematic diagram of FIG. 2(a)) and the cross-sectional area of the cross section of the resin sample in which cavities are filled (the area of the filled portion in the schematic diagram of FIG. 2(b)) are measured. The cross-sectional area of cavity portions in the resin sample (total cross-sectional area of cavity portions (B) in the water-absorbent resin) is calculated by subtracting the cross-sectional area of the resin sample from the cross-sectional area of the resin sample in which cavities are filled. Then, the cavity area ratio of the resin sample is calculated according to Equation (I) shown below. Using this method, the cavity area ratio of the resin sample is measured for each of the four resin samples, and the average value thereof is determined as the cavity area ratio of the water-absorbent resin.

$$\text{Cavity area ratio [\%]} = \{\text{total cross-sectional area } (B)\text{ of cavity portions of the water-absorbent resin}/(\text{total cross-sectional area } (A) \text{ of resin portions of the water-absorbent resin} + \text{total cross-sectional area } (B) \text{ of cavity portions of the water-absorbent resin})\} \times 100. \quad \text{(I)}$$

The method for measuring the cavity area ratio using X-ray computed tomography is more specifically described in the Examples.

In the water-absorbent resin of the present invention, for the water-absorbent resin having a particle diameter of 250 to 500 μm, the liquid flow rate index as calculated by Equation (II) when a physiological saline liquid column flow rate test is performed at 37° C. is 5 to 20. The liquid flow rate index is preferably 6 to 18, and more preferably 8 to 16, from the viewpoint of achieving a water-absorbent resin that exhibits excellent absorption performance and a high permeation rate with respect to liquids to be absorbed, and that effectively reduces liquid leakages, even in an absorbent material using a large amount of the water-absorbent resin.

In the present invention, the liquid flow rate index is calculated by performing the following physiological saline liquid column flow rate test at 37° C.

<Physiological Saline Liquid Column Flow Rate Test at 37° C.>

Particles of the water-absorbent resin are classified in advance with JIS standard sieves. The water-absorbent resin on a sieve with a mesh size of 250 μm that pass through a sieve with a mesh size of 500 μm are used as resin samples. Next, a biocolumn (inside diameter: 25 mm, outlet inside diameter: 3 mm) having a SUS filter (pore diameter: 80 to 100 μm) having a pore diameter of 80 to 100 μm at the bottom is vertically fixed. 0.15 g of a resin sample is uniformly dispersed on the SUS filter, and a 37° C. physiological saline is passed through under a load of 0.3 psi. The liquid flow rate (CPR1) during 10 second period after initiation of liquid flow and the liquid flow rate (CPR2) during 10 second period between 50 seconds and 60 seconds after initiation of liquid flow are measured, and the liquid flow rate is calculated by Equation (II) shown below.

$$\text{Liquid flow rate index} = \{\text{liquid flow rate (CPR2) during 10 second period between 50 seconds and 60 seconds after initiation of liquid flow}/\text{liquid flow rate (CPR1) during 10 second period after initiation of liquid flow}\} \times 100. \quad \text{(II)}$$

It is believed that in the water-absorbent resin of the present invention, because the cavity area ratio is adjusted to 2 to 10%, the amount of the liquid retained in cavity portions (gap portions) of the water-absorbent resin is small, such that the liquid is favorably absorbed by the water-absorbent resin, and the water-absorbent resin of the present invention effectively reduces liquid leakage from the cavity portions. Furthermore, it is believed that in the water-absorbent resin of the present invention, because the liquid flow rate index is adjusted to 5 to 20, the water-absorbent resin exhibits a high permeation rate with respect to liquids to be absorbed and more effectively reduces liquid leakage. As described above, from the viewpoint of reducing the thickness of an absorbent article including a water-absorbent resin, it may be possible to use an absorbent material having a reduced proportion of hydrophilic fibers and an increased proportion of a water-absorbent resin. However, in the case where such a thinned absorbent article is used as, for example, a water-absorbent sheet, if the absorbent material is subjected to a load due to a deformation, a pressure, or the like, the water-absorbent sheet cannot sufficiently prevent leakage of the liquid (liquid to be absorbed). In an absorbent material using a large amount of water-absorbent resin, a so-called "gel blocking phenomenon" tends to occur, and, further, a problem that liquid leakage tends to occur occurs. On the other hand, in the water-absorbent resin of the present invention, the cavity area ratio is adjusted to 2 to 10%, and the liquid flow rate index is adjusted to 5 to 20, so that liquid leakage is effectively suppressed. Thus, even an absorbent material using a large amount of the water-absorbent resin exhibits excellent absorption performance and a high permeation rate with respect to liquids to be absorbed and effectively reduces liquid leakages. Thus, the water-absorbent resin of the present invention can be suitably used for an absorbent article using an absorbent material having an increased proportion of a water-absorbent resin.

The water-absorbent resin of the present invention preferably has a median particle diameter of 200 to 600 μm, more preferably 250 to 500 μm, still more preferably 300 to 450 μm, and even more preferably 350 to 450 μm.

The median particle diameter of the water-absorbent resin can be measured using JIS standard sieves. More specifically, the median particle diameter represents a value as measured using the method described in the Examples.

From the viewpoint of exhibiting excellent absorption performance and a high permeation rate with respect to liquids to be absorbed, and effectively reducing liquid leakages, even in an absorbent material using a large amount of the water-absorbent resin, an upper limit of a physiological saline-retention capacity (g/g) of the water-absorbent resin of the present invention is preferably 35 g/g or less and more preferably 33 g/g or less, and a lower limit thereof is preferably 25 g/g or more and more preferably 26 g/g or more. The range of the physiological saline-retention capacity (g/g) is preferably 25 to 35 g/g, 25 to 33 g/g, 26 to 35 g/g, and 26 to 33 g/g.

The physiological saline-retention capacity is a value measured by the following method, and the method is more specifically described in the Examples.

<Physiological Saline-Retention Capacity>

500 g of a 0.9% by mass aqueous solution of sodium chloride (physiological saline) is weighed out into a 500-ml beaker, and 2.0±0.001 g of the water-absorbent resin is dispersed therein with stirring using a magnetic stirrer bar (8 mm in diameter×30 mm, without a ring) at 600 rpm, so as not to form unswollen lumps. The dispersion is allowed to stand with stirring for 30 minutes, such that the water-absorbent resin is sufficiently swollen. The dispersion is subsequently poured into a cotton bag (Cottonbroad No. 60, 100 mm in width×200 mm in length), and the top of the cotton bag is closed with a rubber band. Then, the cotton bag is dehydrated for 1 minute using a dehydrator set at a centrifugal force of 167 G, and the mass Wa (g) of the dehydrated cotton bag containing the swollen gel is measured. The same procedure is performed without adding the water-absorbent resin, and the mass Wb (g) of the empty cotton bag upon wetting is measured. The physiological saline-retention capacity of the water-absorbent resin is calculated according to the following equation.

Physiological saline-retention capacity (g/g=[Wa−Wb] (g)/mass (g) of the water-absorbent resin.

The water-absorbent resin of the present invention may contain additives suitable for its purpose. Examples of such additives include inorganic powders, surfactants, oxidizing agents, reducing agents, metal chelating agents, radical chain inhibitors, antioxidants, anti-bacterial agents, and deodorizers. For example, when 0.05 to 5 parts by mass of amorphous silica as an inorganic powder is added to 100 parts by mass of the water-absorbent resin, the flowability of the water-absorbent resin can be improved.

The water-absorbent resin of the present invention exhibits excellent absorption performance and a high permeation rate with respect to liquids to be absorbed, and that effectively reduces liquid leakages, even in an absorbent material using a large amount of the water-absorbent resin, and therefore, as described later, the water-absorbent resin of the present invention can be suitably used in an adsorbent material designed to have a proportion of the water-absorbent resin of 50% by mass or more and preferably 70 to 100% by mass in the adsorbent material.

2. Method for Producing Water-Absorbent Resin

The water-absorbent resin of the present invention can be produced by polymerizing a water-soluble ethylenically unsaturated monomer.

To polymerize the water-soluble ethylenically unsaturated monomer, a representative polymerization method such as aqueous solution polymerization, spray droplet polymerization, emulsion polymerization, or reversed phase suspension polymerization is used. In aqueous solution polymerization, polymerization is performed by heating, optionally with stirring, an aqueous solution of the water-soluble ethylenically unsaturated monomer. Examples of methods for controlling the cavity area ratio and the liquid flow rate in aqueous solution polymerization include a method in which a foaming agent, for example, is added to the water-soluble ethylenically unsaturated monomer; and a method in which particles of a water-absorbent resin obtained by aqueous solution polymerization are aggregated. In reversed phase suspension polymerization, polymerization is performed by heating the water-soluble ethylenically unsaturated monomer with stirring in a hydrocarbon dispersion medium. Examples of methods for controlling the cavity area ratio and the liquid flow rate in reversed phase suspension polymerization include a method in which a foaming agent, for example, is added to the first-stage water-soluble ethylenically unsaturated monomer; a method in which the median particle diameter of primary particles obtained in the first-stage reversed phase suspension polymerization is controlled; and a method in which a hydrous gel obtained after the first-stage polymerization is further heated. In the present invention, reversed phase suspension polymerization is preferred from the viewpoint of allowing the polymerization reaction to be precisely controlled, and a wide range of particle diameters to be controlled.

One exemplary method for producing the water-absorbent resin of the present invention will be hereinafter described.

Examples of methods for producing the water-absorbent resin include a method for producing the water-absorbent resin by performing reversed phase suspension polymerization of the water-soluble ethylenically unsaturated monomer in a hydrocarbon dispersion medium, the method including the steps of: performing the polymerization in the presence of a radical polymerization initiator; and post-crosslinking the hydrous gel obtained by the polymerization in the presence of a post-crosslinking agent.

In the method for producing the water-absorbent resin of the present invention, an internal-crosslinking agent may be added, as required, to the water-soluble ethylenically unsaturated monomer to obtain a hydrous gel having an internally crosslinked structure.

<Polymerization Step>

[Water-Soluble Ethylenically Unsaturated Monomer]

Examples of the water-soluble ethylenically unsaturated monomer include (meth)acrylic acid ("acryl" and "methacryl" are herein collectively referred to as "(meth)acryl"; the same applies below) and salts thereof; 2-(meth)acrylamido-2-methylpropanesulfonic acid and salts thereof; non-ionic monomers such as (meth)acrylamide, N,N-dimethyl(meth)acrylamide, 2-hydroxyethyl(meth)acrylate, N-methylol(meth)acrylamide, and polyethylene glycol mono(meth)acrylate; and amino group-containing unsaturated monomers such as N,N-diethyl aminoethyl(meth)acrylate, N,N-diethylaminopropyl(meth)acrylate, and diethylaminopropyl(meth)acrylamide, as well as quaternary compounds thereof. Preferred among these water-soluble ethylenically unsaturated monomers are (meth)acrylic acid and salts thereof, (meth)acrylamide, and N,N-dimethyl (meth)acrylamide, and more preferred are (meth)acrylic acid and salts thereof, from the viewpoint of being readily industrially available. These water-soluble ethylenically unsaturated monomers may be used alone or in combination of two or more.

Among these water-soluble ethylenically unsaturated monomers, acrylic acid and salts thereof are widely used as raw materials of water-absorbent resins. Copolymers of acrylic acid and/or salts thereof with other water-soluble ethylenically unsaturated monomers as mentioned above may also be used. In this case, an acrylic acid and/or a salt thereof as a main water-soluble ethylenically unsaturated monomer is preferably used in an amount of 70 to 100 mol % based on the total amount of water-soluble ethylenically unsaturated monomers.

The water-soluble ethylenically unsaturated monomer is preferably dispersed as an aqueous solution in a hydrocarbon dispersion medium, and then subjected to reversed phase suspension polymerization. When the water-soluble ethylenically unsaturated monomer is in the form of an aqueous solution, the dispersion efficiency in the hydrocarbon dispersion medium can be increased. The concentration of the water-soluble ethylenically unsaturated monomer in the aqueous solution is preferably in the range of 20% by mass to not more than the saturation concentration. The concentration of the water-soluble ethylenically unsaturated monomer is more preferably 55% by mass or less, still more preferably 50% by mass or less, and even more preferably 45% by mass or less. On the other hand, the concentration of the water-soluble ethylenically unsaturated monomer is more preferably 25% by mass or more, still more preferably 28% by mass or more, and even more preferably 30% by mass or more.

When the water-soluble ethylenically unsaturated monomer has an acid group such as (meth)acrylic acid or 2-(meth) acrylamido-2-methylpropanesulfonic acid, the acid group may be neutralized with an alkaline neutralizing agent, as required, before use. Examples of such alkaline neutralizing agents include alkali metal salts such as sodium hydroxide, sodium carbonate, sodium hydrogen carbonate, potassium hydroxide, and potassium carbonate; and ammonia. These alkaline neutralizing agents may be used in the form of aqueous solutions to facilitate the neutralization operation. The above-mentioned alkaline neutralizing agents may be used alone or in combination of two or more.

The degree of neutralization of the water-soluble ethylenically unsaturated monomer with an alkaline neutralizing agent, calculated as the degree of neutralization of all acid groups in the water-soluble ethylenically unsaturated monomer, is preferably 10 to 100 mol %, more preferably 30 to 90 mol %, still more preferably 40 to 85 mol %, and even more preferably 50 to 80 mol %.

[Radical Polymerization Initiator]

Examples of the radical polymerization initiator to be added in the polymerization step include persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide; and azo compounds such as 2,2'-azobis(2-amidinopropane) dihydrochloride, 2,2'-azobis[2-(N-phenylamidino)propane] dihydrochloride, 2,2'-azobis[2-(N-allylamidino)propane]dihydrochloride, 2,2'-azobis {2-[1-(2-hydroxyethyl)-2-imidazolin-2-yl]propane}dihydrochloride, 2,2'-azobis {2-methyl-N-[1,1-his(hydroxymethyl)-2-hydroxyethyl] propionamide}, 2,2'-azobis[2-methyl-N-(2-hydroxyethyl)-propionamide], and 4,4'-azobis(4-cyanovaleric acid). Preferred among these radical polymerization initiators are potassium persulfate, ammonium persulfate, sodium persulfate, and 2,2'-azobis(2-amidinopropane) dihydrochloride, from the viewpoint of being readily available and easy to handle. These radical polymerization initiators may be used alone or in combination of two or more.

The above-mentioned radical polymerization initiators may also be used in combination with reducing agents such as sodium sulfite, sodium hydrogensulfite, ferrous sulfate, and L-ascorbic acid to be used as redox polymerization initiators.

The amount of the radical polymerization initiator to be used may be, for example, 0.00005 to 0.01 mol per mole of the water-soluble ethylenically unsaturated monomer, although not limited thereto. The use of the radical polymerization initiator in the above-defined range of amounts can avoid the occurrence of an abrupt polymerization reaction, and can complete the polymerization reaction in an appropriate time.

[Internal-Crosslinking Agent]

Examples of the internal-crosslinking agent include those that can crosslink the polymer of the water-soluble ethylenically unsaturated monomer to be used, for example: unsaturated polyesters obtained by reacting polyols such as diols and triols, e.g., (poly)ethylene glycol["(poly)" means both cases with and without the prefix "poly"; the same applies below], (poly)propylene glycol, 1,4-butanediol, trimethylolpropane, and (poly)glycerin, with unsaturated acids such as (meth)acrylic acid, maleic acid, and fumaric acid; bisacrylamides such as N,N-methylenebisacrylamide; di or tri(meth)acrylic acid esters obtained by reacting polyepoxides with (meth)acrylic acid; carbamyl di(meth)acrylates obtained by reacting polyisocyanates such as tolylene diisocyanate and hexamethylene diisocyanate with hydroxyethyl (meth)acrylate; compounds having two or more polymerizable unsaturated groups such as allylated starch, allylated cellulose, diallyl phthalate, N,N',N'''-triallylisocyanate, and divinylbenzene; polyglycidyl compounds such as diglycidyl compounds and triglycidyl compounds, e.g., (poly)ethylene glycol diglycidyl ether, (poly)propylene glycol diglycidyl ether, and (poly)glycerin diglycidyl ether; epihalohydrin compounds such as epichlorohydrin, epibromohydrin, and α-methyl epichlorohydrin; compounds having two or more reactive functional groups such as isocyanate compounds, e. 2,4-tolylene diisocyanate and hexamethylene diisocyanate; and oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol. Among these internal-crosslinking agents, polyglycidyl compounds are preferably used, diglycidyl ether compounds are more preferably used, and (poly)ethylene glycol diglycidyl ether, (poly)propylene glycol diglycidyl ether, and (poly)glycerin diglycidyl ether are still more preferably used. These internal-crosslinking agents may be used alone or in combination of two or more.

The amount of the internal-crosslinking agent to be used is preferably 0.000001 to 0.02 mol, more preferably 0.00001 to 0.01 mol, still more preferably 0.00001 to 0.005 mol, and even more preferably 0.00001 to 0.002 mol, per mole of the water-soluble ethylenically unsaturated monomer.

[Hydrocarbon Dispersion Medium]

Examples of the hydrocarbon dispersion medium include $C_{6-8}$ aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane, and aromatic hydrocarbons such as benzene, toluene, and xylene. Among these hydrocarbon dispersion media, n-hexane, n-heptane, and cyclohexane, which are readily industrially available, stable in quality, and inexpensive, are particularly suitably used. These hydrocarbon dispersion media may be used alone or in combination of two or more. Examples of mixtures of hydrocarbon dispersion media include commercially available products such as Exxsol Heptane (from Exxon Mobil Corporation; containing 75 to 85% by mass of heptane and its isomeric hydrocarbons). The use of such a commercially available product also leads to favorable results.

The amount of the hydrocarbon dispersion medium to be used is preferably 100 to 1500 parts by mass, and more preferably 200 to 1400 parts by mass, per 100 parts by mass of the first-stage water-soluble ethylenically unsaturated monomer, from the viewpoint of homogeneously dispersing the water-soluble ethylenically unsaturated monomer, and facilitating control of the polymerization temperature. As described below, reversed phase suspension polymerization is performed in a single stage or two or more multiple stages. The first-stage polymerization as mentioned above refers to the first-stage polymerization reaction in single-stage polymerization or multi-stage polymerization (the same applies below).

[Dispersion Stabilizer]

(Surfactant)

In reversed phase suspension polymerization, a dispersion stabilizer may be used to improve the dispersion stability of the water-soluble ethylenically unsaturated monomer in the hydrocarbon dispersion medium. A surfactant may be used as such a dispersion stabilizer.

Examples of the surfactant include sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkyl allyl formaldehyde condensate polyoxyethylene ethers, polyoxyethylene-polyoxypropylene block copolymers, polyoxyethylene polyoxypropyl alkyl ethers, polyethylene glycol fatty acid esters, alkyl glucosides, N-alkyl glyconamides, polyoxyethylene fatty acid amides, polyoxyethylene alkylamines, polyoxyethylene alkyl ether phosphates, and polyoxyethylene alkyl allyl ether phosphates. Among these surfactants, sucrose fatty acid esters, polyglycerin fatty acid esters, and sorbitan fatty acid esters are particularly preferably used, from the viewpoint of dispersion stability of the monomer. These surfactants may be used alone or in combination of two or more.

The amount of the surfactant to be used is preferably 0.1 to 30 parts by mass, and more preferably 0.3 to 20 parts by mass, per 100 parts by mass of the first-stage water-soluble ethylenically unsaturated monomer.

(Polymeric Dispersion Agent)

A polymeric dispersion agent may be used in combination with the above-described surfactant, as a dispersion stabilizer to be used in reversed phase suspension polymerization.

Examples of the polymeric dispersion agent include maleic anhydride modified polyethylene, maleic anhydride modified polypropylene, maleic anhydride modified ethylene-propylene copolymers, maleic anhydride modified EPDM (ethylene-propylene-diene terpolymers), maleic anhydride modified polybutadiene, maleic anhydride-ethylene copolymers, maleic anhydride-propylene copolymers, maleic anhydride-ethylene-propylene copolymers, maleic anhydride-butadiene copolymers, polyethylene, polypropylene, ethylene-propylene copolymers, oxidized polyethylene, oxidized polypropylene, oxidized ethylene-propylene copolymers, ethylene-acrylic acid copolymers, ethyl cellulose, and ethyl hydroxyethyl cellulose. Among these polymeric dispersion agents, maleic anhydride modified polyethylene, maleic anhydride modified polypropylene, maleic anhydride modified ethylene-propylene copolymers, maleic anhydride-ethylene copolymers, maleic anhydride-propylene copolymers, maleic anhydride-ethylene-propylene copolymers, polyethylene, polypropylene, ethylene-propylene copolymers, oxidized polyethylene, oxidized polypropylene, and oxidized ethylene-propylene copolymers are particularly preferably used, from the viewpoint of dispersion stability of the monomer. These polypmeric dispersion agents may be used alone or in combination of two or more.

The amount of the polymeric dispersion agent to be used is preferably 0.1 to 30 parts by mass, and more preferably 0.3 to 20 parts by mass, per 100 parts by mass of the first-stage water-soluble ethylenically unsaturated monomer.

[Other Components]

In the method for producing the water-absorbent resin, other components may be added, as desired, to the aqueous solution containing the water-soluble ethylenically unsaturated monomer to be subjected to reversed phase suspension polymerization. Various additives such as thickeners, foaming agents, and chain transfer agents may be added as other components.

(Thickener)

By way of example, a thickener may be added to the aqueous solution containing the water-soluble ethylenically unsaturated monomer to be subjected to reversed phase suspension polymerization. When a thickener is thus added to adjust the viscosity of the aqueous solution, the median particle diameter of the particles obtained by reversed phase suspension polymerization can be controlled.

Examples of usable thickeners include hydroxyethylcellulose, hydroxypropylcellulose, methylcellulose, carboxymethylcellulose, polyacrylic acid, (partially) neutralized polyacrylic acid, polyethylene glycol, polyacrylamide, polyethyleneimine, dextrin, sodium alginate, polyvinyl alcohol, polyvinylpyrrolidone, and polyethylene oxide. For a fixed stirring rate during the polymerization, the higher the viscosity of the aqueous solution containing the water-soluble ethylenically unsaturated monomer, the larger the median particle diameter of the primary particles and/or secondary particles of the resulting particles tends to be.

(Foaming Agent)

By way of example, a foaming agent may be added to the aqueous solution containing the water-soluble ethylenically unsaturated monomer to be subjected to reversed phase suspension polymerization. When a foaming agent is thus added to introduce foam into the aqueous solution, the cavity a ratio and the liquid flow rate of the particles obtained by reversed phase suspension polymerization can be controlled. Various foaming agents such as carbonates and hydrogencarbonates may be used as the foaming agent.

[Reversed Phase Suspension Polymerization]

To perform reversed phase suspension polymerization, for example, the aqueous monomer solution containing the water-soluble ethylenically unsaturated monomer is dispersed in a hydrocarbon dispersion medium, in the presence of a dispersion stabilizer. Here, so long as the dispersion stabilizer (a surfactant or a polymeric dispersion agent) is added before the beginning of the polymerization reaction, it may be added either before or after the aqueous monomer solution is dispersed in the hydrocarbon dispersion medium.

In particular, from the viewpoint of readily reducing the amount of remaining hydrocarbon dispersion medium in the resulting water-absorbent resin, it is preferred to disperse the aqueous monomer solution in the hydrocarbon dispersion medium in which a polymeric dispersion agent is dispersed, followed by dispersing a surfactant therein, and then perform polymerization.

Such reversed phase suspension polymerization can be performed in a single stage or two or more multiple stages. From the viewpoint of enhancing productivity reversed phase suspension polymerization is preferably performed in two or three stages.

Reversed phase suspension polymerization with two or more multiple stages may be performed as follows: the first-stage reversed phase suspension polymerization is performed; subsequently, a water-soluble ethylenically unsaturated monomer is added to the reaction mixture obtained by the first-stage polymerization reaction and mixed, and reversed phase suspension polymerization in the second and subsequent stages is performed in the same manner as in the first stage. In reversed phase suspension polymerization in each of the second and subsequent stages, in addition to the water-soluble ethylenically unsaturated monomer, a radical polymerization initiator is preferably added within the above-described range of molar ratios of each of the components relative to the water-soluble ethylenically unsaturated monomer, based on the amount of the water-soluble ethylenically unsaturated monomer added during reversed phase suspension polymerization in each of the second and subsequent stages. In the second and subsequent stages of polymerization, an internal-crosslinking agent may also be added, as required, to the water-soluble ethylenically unsaturated monomer.

The reaction temperature during the polymerization reaction is preferably 20 to 110° C., and more preferably 40 to 90° C., from the viewpoint of allowing the polymerization to proceed quickly to reduce the polymerization time for improved economical efficiency, and readily removing the heat of polymerization to perform a smooth reaction.

During the production of the water-absorbent resin of the present invention, the system in which the hydrous gel is dispersed in the hydrocarbon dispersion medium after the first-stage reversed phase suspension polymerization may be heated, as required, by applying external energy such as heat. The heating temperature is preferably 50 to 100° C., and more preferably 60 to 90° C. The heating time is preferably 0.1 to 3 hours.

The aqueous monomer solution may be stirred with any of various well-known stirring blades. Specific examples of usable stirring blades include propeller blades, paddle blades, anchor blades, turbin blades, Pfaudler blades, ribbon blades, FULLZONE blades (from Shinko Pantec Co., Ltd.), MAXBLEND blades (from Sumitomo Heavy Industries, Ltd.), and SUPERMIX blades (from Satake Chemical Equipment Mfg., Ltd.). The median particle diameter of the primary particles obtained in the first-stage polymerization can be controlled by adjusting the stirring rate in the first-stage reversed phase suspension polymerization. The stirring rate can be adjusted, for example, by adjusting the rotational speed of stirring.

In the method for producing the water-absorbent resin of the present invention, the above-described cavity area ratio can be controlled to 10% or less, by, for example, adjusting the amount of the radical polymerization initiator and the amount of the internal-crosslinking agent to be added to the water-soluble ethylenically unsaturated monomer during reversed phase suspension polymerization, by controlling the median particle diameter of the primary particles in the first-stage polymerization, and by heating the hydrous gel after the first-stage polymerization. These procedures may be performed alone or in combination.

<Post-Crosslinking Step>

Next, the water-absorbent resin of the present invention is obtained by post-crosslinking the hydrous gel having an internally crosslinked structure obtained by polymerizing the water-soluble ethylenically unsaturated monomer, using a post-crosslinking agent (post-crosslinking reaction). The post-crosslinking reaction is preferably preformed in the presence of a post-crosslinking agent, after the polymerization of the water-soluble ethylenically unsaturated monomer. When the hydrous gel having an internally crosslinked structure is thus subjected to the post-crosslinking reaction after the polymerization, a water-absorbent resin can be achieved in which the crosslinking density in the vicinity of the surface has been increased to improve various kinds of performance such as the water-absorption capacity under a load.

Examples of the post-crosslinking agent include compounds having two or more reactive functional groups. Examples of the post-crosslinking agent include polyols such as ethylene glycol, propylene glycol, 1,4-butanediol, trimethylolpropane, glycerin, poly oxyethylene glycol, polyoxypropylene glycol, and polyglycerin; polyglycidyl compounds such as (poly)ethylene glycol diglycidyl ether, (poly) glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromohydrin, and α-methylepichlorohydrin; isocyanate compounds such as 2,4-tolylene diisocyanate and hexamethylene diisocyanate; oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Preferred among these post-crosslinking agents are polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether. These post-crosslinking agents may be used alone or in combination of two or more.

The amount of the post-crosslinking agent to be used is preferably 0.00001 to 0.01 mol, more preferably 0.00005 to 0.005 mol, and still more preferably 0.0001 to 0.002 mol, per mole of the water-soluble ethylenically unsaturated monomer subjected to polymerization. In the case of multistage reversed-phase suspension polymerization by two or more stages, the amount of the water-soluble ethylenically unsaturated monomer, which is the basis of the amount of the post-crosslinking agent to be used, is the total amount of the water-soluble ethylenically unsaturated monomer used in each stage.

The post-crosslinking agent may be added as is or as an aqueous solution. As required, a solution of the post-crosslinking agent in a hydrophilic organic solvent may be added. Examples of such hydrophilic organic solvents include lower alcohols such as methyl alcohol, ethyl alcohol, n-propyl alcohol, and isopropyl alcohol; ketones such as acetone and methyl ethyl ketone; ethers such as diethyl ether, dioxane, and tetrahydrofuran; amides such as N,N-dimethylformamide; and sulfoxides such as dimethylsulfoxide. These hydrophilic organic solvents may be used alone, in combination of two or more, or as a mixture with water.

The post-crosslinking agent may be added after the polymerization reaction of the water-soluble ethylenically unsaturated monomer is substantially completed. The post-crosslinking agent is preferably added in the presence of 1 to 400 parts by mass of water, more preferably 5 to 200 parts by mass of water, still more preferably 10 to 100 parts by mass of water, and even more preferably 20 to 60 parts by mass of water, per 100 parts by mass of the water-soluble ethylenically unsaturated monomer. The amount of water herein refers to the total amount of the water contained in the reaction system and the water that is used, as required, during the addition of the post-crosslinking agent.

The reaction temperature during the post-crosslinking reaction is preferably 50 to 250° C., more preferably 60 to 180° C., still more preferably 60 to 140° C., and even more preferably 70 to 120° C. The reaction time of the post-crosslinking reaction is preferably 1 to 300 minutes, and more preferably 5 to 200 minutes.

<Drying Step>

The method for producing the water-absorbent resin of the present invention may include, after performing reversed phase suspension polymerization as described above, a drying step of adding external energy such as heat to remove the water, hydrocarbon dispersion medium, and the like by distillation. To remove the water in the hydrous gel after reversed phase suspension polymerization, the system in which the hydrous gel is dispersed in the hydrocarbon dispersion medium is heated to distill the water and the hydrocarbon dispersion medium out of the system by azeotropic distillation. Here, if the distilled hydrocarbon dispersion medium only is returned into the system, continuous azeotropic distillation can be performed. In this case, the temperature within the system during drying is maintained at a temperature not higher than the azeotropic temperature with the hydrocarbon dispersion medium, which is preferable from the viewpoint of inhibiting deterioration of the resin. Subsequently, the water and the hydrocarbon dispersion medium are distilled off to obtain particles of the water-absorbent resin. By controlling the treatment conditions for the drying step after the polymerization to adjust the amount of water to be removed, various kinds of performance of the resulting water-absorbent resin can be controlled.

In the drying step, the drying treatment by distillation may be performed under atmospheric pressure or reduced pressure. The drying treatment may also be performed in a stream of nitrogen or the like, from the viewpoint of enhancing the drying efficiency. When the drying treatment is performed under atmospheric pressure, the drying temperature is preferably 70 to 250° C., more preferably 80 to 180° C., still more preferably 80 to 140° C., and even more preferably 90 to 130° C. When the drying treatment is performed under reduced pressure, the drying temperature is preferably 40 to 160° C., and more preferably 50 to 110° C.

When the post-crosslinking step with a post-crosslinking agent is performed after polymerization of the monomer by reversed phase suspension polymerization, the drying step by distillation is performed as described above, after the completion of the post-crosslinking step. Alternatively, the post-crosslinking step and the drying step may be performed simultaneously.

Furthermore, various additives such as chelating agents, reducing agents, oxidizing agents, anti-bacterial agents, and deodorizers may be added, as required, to the water-absorbent resin, after polymerization, during drying, or after drying.

3. Absorbent Material and Absorbent Article

The water-absorbent resin of the present invention constitutes an absorbent material to be used for hygienic materials such as sanitary items and disposable diapers, and is suitably used for an absorbent article including the absorbent material.

Here, the absorbent material including the water-absorbent resin is composed of, for example, the water-absorbent resin and hydrophilic fibers. Examples of structures of the absorbent material include a mixed dispersion obtained by mixing the water-absorbent resin and hydrophilic fibers to give a homogeneous composition; a sandwich structure in which the water-absorbent resin is sandwiched between layered hydrophilic fibers and a structure in which the water-absorbent resin and hydrophilic fibers are wrapped in tissue paper. The absorbent material may also contain other components such as thermally fusible synthetic fibers for enhancing the shape retention properties of the absorbent material, a hot melt adhesive, and an adhesive binder such as an adhesive emulsion. The water-absorbent resin of the present invention can also be used in an absorbent material that is substantially free of hydrophilic fibers (i.e., the content of hydrophilic fibers in the absorbent material is 0% by mass). Examples of absorbent materials substantially free of hydrophilic fibers include water-absorbent sheets.

Examples of hydrophilic fibers include cellulose fibers such as cotton-like pulp made from wood, mechanical pulp, chemical pulp, and semi-chemical pulp; artificial cellulose fibers such as rayon and acetate; and fibers made of synthetic resins such as hydrophilized polyamide, polyester, and polyolefin.

The absorbent material including the water-absorbent resin can be held between a liquid-permeable sheet (top sheet) that allows a liquid to pass through and a liquid-impermeable sheet (back sheet) that does not allow a liquid to pass through, to obtain an absorbent article. The liquid-permeable sheet is positioned on the side of the absorbent article that is brought into contact with the body, and the liquid-impermeable sheet is positioned opposite to the side that is brought into contact with the body.

Examples of the liquid-permeable sheet include air-through, spunbond, chemical bond, or needle punch non-woven fabrics made of fibers of polyethylene, polypropylene, polyester, or the like, and porous synthetic resin sheets. Examples of the liquid-impermeable sheet include synthetic resin films made of resins such as polyethylene, polypropylene, and polyvinyl chloride.

Since the water-absorbent resin of the present invention exhibits excellent absorption performance and a high permeation rate with respect to liquids to be absorbed, and effectively reduces liquid leakages, even in an absorbent material using a large amount of the water-absorbent resin, the content of the water-absorbent resin in the absorbent material is preferably 50% by mass or more, and more preferably 70 to 100% by mass.

The water-absorbent resin of the present invention constitutes, together with hydrophilic fibers, an adsorbent material, whereby the water-absorbent resin exhibits excellent absorption performance and a high permeation rate with respect to liquids to be absorbed, and effectively reduces liquid leakages even when the proportion of the hydrophilic fibers in the absorbent material is preferably 50% by mass or less, and more preferably 0 to 30% by mass.

When the water-absorbent resin of the present invention is used in an adsorbent material, a thin absorbent article having a thickness that is preferably 5 mm or less, more preferably 3 mm or less, for example, can be achieved.

EXAMPLES

Hereinafter, the present invention will be described in detail with reference to examples and comparative examples. However, the present invention is not limited to the examples.

Water-absorbent resins obtained in the following examples and comparative examples were evaluated using the tests described below. Each of the testing methods for evaluation will be hereinafter described.

<Measurement of Cavity Area Ratio Using X-ray Computed Tomography>

Particles of the water-absorbent resin were classified in advance with JIS standard sieves. Four particles were randomly selected from particles of the water-absorbent resin on a sieve with a mesh size of 180 μm that passed through a sieve with a mesh size of 600 μm, and these particles were used as resin samples. The resin samples were placed on a sample stage of an X-ray computer tomography apparatus (MicroXCT-400 from Xradia Inc.), and cross-sectional image data were acquired using X-ray computer tomography. Next, for each of the resin samples, shapes at given angles or given horizontal and vertical cross sections were observed using image analysis software (myVGL from Volume Graphics GmbH).

Here, from given cross sections in horizontal directions (x- and y-directions) and a vertical direction (z-direction) with respect to the mounting surface of the sample stage, a horizontal or vertical cross-sectional image having a maximum distance between given two points on the contour of each of the resin samples was selected. Specifically, as shown in the schematic diagram of FIG. 1, for each of the three directions, x-, y-, and z-directions, that are perpendicular to one another, cross-sectional images of a resin sample 11 on the sample stage 10 were acquired first. Subsequently, for each of these directions, one cross-sectional image having the longest particle length w (see FIGS. 1 and 2) of the resin sample (i.e., a cross-sectional image taken in a position where the particle length of the resin sample was the longest) was selected. Then, a cross-sectional image having the longest particle length w of the resin sample of these three cross-sectional images was selected.

More specifically, initially, cross sections (z-x sections) of slices of the resin sample were observed in y-direction while shifting the position in y-direction with respect to the mounting surface of the sample stage, and a z-x cross section having the longest particle length w of the resin sample (see FIGS. 1 and 2) was acquired. Similarly, cross sections (a z-y cross section and an x-y cross section) having the longest particle length of the resin sample as observed in x- and z-directions were acquired. Then, a cross section having the longest particle length w of the resin sample of these three cross sections was selected.

Next, the cavity area ratio was calculated using this cross-sectional image. By means of general-purpose image processing software (NanoHunter NS2K-Pro/Lt from Nanosystem Corporation), the cross-sectional area of the resin sample (total cross-sectional area of resin portions (A) in the water-absorbent resin) (the area of the filled portions in the schematic diagram of FIG. 2(a)) and the cross-sectional area of the cross section of the resin sample in which cavities are filled (the area of the filled portion in the schematic diagram of FIG. 2(b)) were measured. The cross-sectional area of cavity portions in the resin sample (total cross-sectional area of cavity portions (B) in the water-absorbent resin) was calculated by subtracting the cross-sectional area of the resin sample from the cross-sectional area of the resin sample in which cavities are filled. Then, the cavity area ratio of the resin sample was calculated according to Equation (1) shown below. Using this method, the cavity area ratio of the resin sample was measured for each of the four resin samples, and the average value thereof was determined as the cavity area ratio of the water-absorbent resin.

$$\text{Cavity area ratio [\%]} = \{\text{total cross-sectional area } (B) \text{ of cavity portions of the water-absorbent resin}/(\text{total cross-sectional area } (A) \text{ of resin portions of the water-absorbent resin} + \text{total cross-sectional area } (B) \text{ of cavity portions of the water-absorbent resin})\} \times 100. \quad (I)$$

The conditions for X-ray computer tomography were as follows:

Apparatus: MicroXCT-400 (Xradia Inc.)
X-ray tube voltage: 80 kV
X-ray tube current: 122 μA
Optical lens: 10 times
Irradiation time: 0.8 sec
Pixel size: 2.149 μm
X-ray source-to-sample distance: 29.1533 mm
Detector-to-sample distance: 7.3723 mm
Imaging range: −90° to 90°
Image analyzer: my VGL 2.2 (Volume Graphics GmbH)

<Median Particle Diameter>

JIS standard sieves having mesh sizes of 850 μm, 600 μm, 500 μm, 425 μm, 300 μm, 250 μm, and 150 μm, and a receiving tray were combined in that order from the top.

50 g of the water-absorbent resin was placed on the top sieve of the combined sieves, and shaken for 20 minutes with a Ro-Tap shaker to conduct classification. After the classification, the particle size distribution was determined by calculating the mass of the water-absorbent resin remaining on each sieve as the mass percentage relative to the total mass. With regard to this particle size distribution, the mass percentage of the water-absorbent resin remaining on each sieve was integrated in descending order of particle diameter. Thereby, the relationship between the sieve mesh size and the integrated value of the mass percentage of the water-absorbent resin remaining on each sieve was plotted on logarithmic probability paper. The plots on the probability paper were connected with straight lines, and a particle diameter equivalent to 50% by mass of the integrated mass percentage was determined as the median particle diameter.

<Physiological Saline Liquid Column Flow Rate Test at 37° C.>

Particles of the water-absorbent resin are classified in advance with JIS standard sieves. The particles of the water-absorbent resin on a sieve with a mesh size of 250 μm that pass through a sieve with a mesh size of 500 μm were used as resin samples. Next, a biocolumn (inside diameter: 25 mm, outlet inside diameter: 3 mm) having a SUS filter (pore diameter: 80 to 100 μm) having a pore diameter of 80 to 100 μm at the bottom is vertically fixed. 0.15 g of a resin sample was uniformly dispersed on the SUS filter, and a 37° C. physiological saline was passed through under a load of 0.3 psi. The liquid flow rate (CPR1) during 10 second period after initiation of liquid flow and the liquid flow rate (CPR2) during 10 second period between 50 seconds and 60 seconds after initiation of liquid flow were measured, and the liquid flow rate was calculated by Equation (II) shown below.

$$\text{Liquid flow rate index} = \{\text{liquid flow rate (CPR2) during 10 second period between 50 seconds and 60 seconds after initiation of liquid flow} / \text{liquid flow rate (CPR1) during 10 second period after initiation of liquid flow}\} \times 100. \quad (II)$$

<Physiological Saline-Retention Capacity>

500 g of a 0.9% by mass aqueous solution of sodium chloride (physiological saline) was weighed out into a 500-ml beaker, and 2.0±0.001 g of the water-absorbent resin was dispersed therein with stirring using a magnetic stirrer bar (8 mm in diameter×30 mm, without a ring) at 600 rpm, so as not to form unswollen lumps. The dispersion was allowed to stand with stirring for 30 minutes, such that the water-absorbent resin was sufficiently swollen. The dispersion was subsequently poured into a cotton bag (Cotton-broad No. 60, 100 mm in width×200 mm in length), and the top of the cotton bag was closed with a rubber band. Then, the cotton bag was dehydrated for 1 minute using a dehydrator (product number: H-122 from Kokusan Co., Ltd.) set at a centrifugal force of 167 G, and the mass Wa (g) of the dehydrated cotton bag containing the swollen gel was measured. The same procedure was performed without adding the water-absorbent resin, and the mass Wb (g) of the empty cotton bag upon wetting was measured. The physiological saline-retention capacity of the water-absorbent resin was calculated according to the following equation:

Physiological saline-retention capacity (g/g)=[Wa−Wb](g)/mass (g) of the water-absorbent resin <Evaluation of Absorbent Article>
(1) Preparation of Artificial Urine 60 g of sodium chloride, 1.8 g of calcium chloride dihydrate, 3.6 g of magnesium chloride hexahydrate, and a suitable amount of distilled water were placed in a 10-L container, and completely dissolved. Next, 0.02 g of polyoxyethylene nonylphenyl ether was added, and then distilled water was added to adjust the mass of the entire aqueous solution to 6000 g. Lastly, the resulting product was colored with a small amount of Blue No. 1 to obtain artificial urine.
(2) Preparation of Absorbent Article 12 g of the water-absorbent resin and 1.3 g of crushed pulp (Rayfloc from Rayonier Inc.) were used and were uniformly mixed by air papermaking, and thus an absorbent material core in the shape of a sheet of 40 cm×12 cm was produced. Next, while the absorbent material core was placed between two tissue papers, each of which had the same size as the absorbent material core and a basis weight of 16 g/m², the absorbent material core was all over pressed with a load of 196 kPa for 30 seconds to prepare an absorbent material. Furthermore, on the upper surface of the absorbent material, a polyethylene-polypropylene air-through type porous liquid permeable sheet having the same size as the absorbent material and a basis weight of 22 g/m² was arranged, and a polyethylene liquid impermeable sheet having the same size and the same basis weight was arranged on the lower surface of the absorbent material and the absorbent material was sandwiched therebetween to form an absorbent article.
(3) Measurement of Liquid Permeation Time of Absorbent Article and Confirmation of Liquid Leakage Next, an absorbent article was placed on a horizontal table. A measurement device equipped with a cylinder for introducing a liquid, having an inside diameter of 3 cm was placed on a central part of the absorbent article. 50 ml of artificial urine was introduced into the cylinder at a time, and simultaneously a time until when the artificial urine completely disappeared in the cylinder was measured with a stopwatch and was defined as first liquid permeation time (sec). Subsequently, the cylinder was removed and the absorbent article was stored as it was. After 30 minutes and 60 minutes from the first artificial urine introduction, the measurement instrument was also placed on the same part as in the first time and the same operation was carried out to measure second and third liquid permeation times (sec). Total time of the first time to third time was defined as total of liquid permeation time.

The presence or absence of a liquid leakage from the absorbent article was confirmed by visual observation at the time of the measurement of the liquid permeation time.

<Production of Water-absorbent Resin>

Example 1

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 600 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the water bath was adjusted to 80° C., and the reaction mixture was heated for 60 minutes. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.129 g (0.475 mmol) of 2,2'-azobis(2-amidinopropane) dihydrochloride as an azo-based compound and 0.0116 g (0.067 mmol) of ethylene glycol diglycidyl ether as an internal-crosslinking agent were added and dissolved. As a result, a second-stage aqueous monomer solution was prepared.

The rotation speed of the stirrer was changed to 1000 rpm, and then the atmosphere within the separable flask was cooled. The entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes. After the second-stage polymerization, the reaction mixture in the flask was heated in an oil bath at 125° C. to distill 224 g of water out of the system while refluxing n-heptane into the system by azeotropic distillation of water and n-heptane. Then. 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the Mixture was dried to obtain a resin powder. The resin powder was passed through a sieve with a mesh size of 850 μm to obtain 239.0 g of a water-absorbent resin with a median particle diameter of 390 μm in which spherical particles were aggregated.

Example 2

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 500 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the water bath was adjusted to 80° C., and the reaction mixture was heated for 120 minutes. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.129 g (0.475 mmol) of 2,2'-azobis(2-amidinopropane) dihydrochloride as an azo-based compound and 0.0116 g (0.067 mmol) of ethylene glycol diglycidyl ether as an internal-crosslinking agent were added and dissolved. As a result, a second-stage aqueous monomer solution was prepared.

The rotation speed of the stirrer was changed to 1000 rpm, and then the atmosphere within the separable flask was cooled. The entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes. After the second-stage polymerization, the reaction mixture in the flask was heated in an oil bath at 125° C. to distill 227 g of water out of the system while refluxing n-heptane by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 242.0 g of a water-absorbent resin with a median particle diameter of 380 μm in which spherical particles were aggregated.

Example 3

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 600 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the water bath was adjusted to 80° C., and the reaction mixture was heated for 120 minutes. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.129 g (0.475 mmol) of 2,2'-azobis(2-amidinopropane) dihydrochloride as an azo-based compound and 0.0116 g (0.067 mmol) of ethylene glycol diglycidyl ether as an internal-crosslinking agent were added and dissolved. As a result, a second-stage aqueous monomer solution was prepared.

The rotation speed of the stirrer was changed to 1000 rpm, and then the atmosphere within the separable flask was cooled. The entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes. After the second-stage polymerization, the reaction mixture in the flask was heated in an oil bath at 125° C. to distill 227 g of water out of the system while refluxing n-heptane into the system by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 241.0 g of a water-absorbent resin with a median particle diameter of 380 μm in which spherical particles were aggregated.

Comparative Example 1

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was healed with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 600 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the rotation speed of the stirrer was changed to 1000 rpm, and in an oil bath at 125° C., 23 g of water was distilled out of the system while refluxing n-heptane by azeotropic distillation of water and n-heptane, so that first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.11 g (0.00041 mol) of 2,2'-azobis(2-amidinopropane) dihydrochloride as an azo-based compound and 0.0116 g (0.000067 mol) of ethylene glycol diglycidyl ether as an internal-crosslinking agent were added and dissolved. As a result, a second-stage aqueous monomer solution was prepared.

The atmosphere within the separable flask was cooled. Then, entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes.

After the second-stage polymerization, the reaction mixture in the flask was heated in an oil bath at 125° C. to distill 208 g of water out of the system while refluxing n-heptane into the system by azeotropic distillation of waster and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 238.0 g of a water-absorbent resin with a median particle diameter of 390 μm in which spherical particles were aggregated.

Comparative Example 2

A 2-L cylindrical round-bottomed separable flask having an inside diameter of 110 mm, and equipped with a reflux condenser, a dropping funnel, and a stirrer having stirring blades composed of four inclined paddle blades with a blade diameter of 50 mm was prepared. This flask was charged with 195.4 g (2.71 mol) of acrylic acid, then 135.1 g of ion-exchanged water was added while stirring the inside of the flask, and 357.9 g of 30% by mass sodium hydroxide was added dropwise with external cooling Thereafter, 104.7 g (1.45 mol) of acrylic acid was added to prepare a partially neutralized acrylic acid solution having a degree of neutralization of 65 mol %.

43.7 g of an aqueous solution of 2% polyethylene glycol diacrylate (average repeating unit of ethylene oxide: 9) as an internal-crosslinking agent solution and 180.9 g of ion-exchanged water were mixed with 780 g of the above partially neutralized acrylic acid solution having a degree of neutralization of 65 mol % to prepare an aqueous monomer solution.

The aqueous monomer solution was weighed in an amount of 745.5 g in a vat (made of stainless steel: diameter 188 mm, height 60 mm), and nitrogen was blown such that dissolved oxygen in the solution was 0.1 ppm or less.

Subsequently, the temperature of the above aqueous solution was adjusted to 18° C. under a nitrogen atmosphere, and then 1.19 g (0.25 mmol) of a 5% by mass aqueous solution of sodium persulfate, 1.19 g (0.22 mmol) of a 5% by mass aqueous solution of 2,2'-azobis(2-amidinopropane) dihydrochloride, 1.12 g (0.032 mmol) of 0.5% by mass aqueous L-ascorbic acid solution, and 1.27 g (0.13 mmol) of 0.35% by mass aqueous hydrogen peroxide solution were sequentially added under stirring.

Polymerization started immediately after addition of hydrogen peroxide, and after 9 minutes, the temperature of the monomer reached the peak temperature. The peak temperature was 89° C. Subsequently, the vat was immersed in a water bath at 80° C. and heated for 10 minutes to obtain a clear hydrous gel.

The hydrous gel was crushed by a 1 L double-arm kneader (IRIS SHOKAI Co., Ltd., tabletop kneader PNV-1), and then dried at 180° C. for 30 minutes to obtain a dried product. The dried product was pulverized by a pulverizer (Retsch Gmbh & Co. Kg, Rotor beater mill SR300), and particles remaining on a sieve with a mesh size of 106 μm that passed through a sieve with a mesh size of 500 μm were classified to obtain 716 g of resin powder.

30 g of the resin powder obtained above was mixed with a composition comprising 0.015 g (0.086 mmol) of ethylene glycol diglycidyl ether, 0.3 g (3.94 mmol) of propylene glycol, 0.9 g of water and 0.3 g (4.99 mmol) of isopropyl alcohol and then held at 180° C. for 40 minutes to obtain 28.9 g of a water-absorbent resin having a median particle diameter of 320 μm.

Comparative Example 3

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 500 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the rotation speed of the stirrer was changed to 1000 rpm, and in an oil bath at 125° C., 69 g of water was distilled out of the system while refluxing n-heptane into the system by azeotropic distillation of water and n-heptane, so that first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.11 g (0.00041 mol) of 2,2'-azobis(2-amidinopropane) dihydrochloride as an azo-based compound and 0.0116 g (0.000067 mol) of ethylene glycol diglycidyl ether as an internal-crosslinking agent were added and dissolved. As a result, a second-stage aqueous monomer solution was prepared.

The atmosphere within the separable flask was cooled. Then, the entire amount of the second-stage aqueous monomer solution was added to the first-stage polymerization slurry, and the atmosphere within the system adjusted to 26° C. was sufficiently replaced with nitrogen. The flask was again immersed in a water bath at 70° C. and heated, and the second-stage polymerization was performed for 30 minutes.

After the second-stage polymerization, the reaction mixture in the flask was heated in an oil bath at 125° C. to distill 169 g of water out of the system while refluxing n-heptane into the system by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 238.0 g of a water-absorbent resin with a median particle diameter of 370 μm in which spherical particles were aggregated.

Comparative Example 4

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 500 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the water bath was adjusted to 80° C., and the reaction mixture was heated for 60 minutes. As a result, first-stage polymerization slurry was obtained. Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.129 g (0.475 mmol) of 2,2'-azobis (2-amidinopropane) dihydrochloride as an azo-based compound and 0.0116 g (0.067 mmol) of ethylene glycol diglycidyl ether as an internal-crosslinking agent were added and dissolved. As a result, a second-stage aqueous monomer solution was prepared.

The rotation speed of the stirrer was changed to 1000 rpm, and then the atmosphere within the separable flask was cooled. The entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes. After the second-stage polymerization, the reaction mixture in the flask was heated in an oil bath at 125° C. to distill 239 g of water out of the system while refluxing n-heptane by azeotropic distillation of water and n-heptane. Then, 4.42 g (0.51 mmol) of a by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 244.0 g of a water-absorbent resin with a median particle diameter of 400 μm in which spherical particles were aggregated.

Comparative Example 5

A cylindrical round-bottomed separable flask having an inside diameter of 100 mm, and equipped with a reflux condenser, a dropping funnel, a nitrogen gas inlet tube, and a stirrer having stirring blades (with a surface coated with a fluororesin) composed of two sets of four inclined paddle blades with a blade diameter of 50 mm was prepared. 479 g of n-heptane was charged into the flask, and 1.10 g of hexaglycerol diester (Sakamoto Yakuhin kogyo Co., Ltd., SY-Glyster SS-5S) having an HLB of 9.6 was added thereto as a surfactant. The contents were heated to 50° C. so that the surfactant was dissolved therein, and then the temperature was cooled to 40° C.

Separately, 92 g (1.03 mol) of a 80.5% by mass acrylic acid aqueous solution was placed in a 500-mL Erlenmeyer flask, 147.7 g of a 20.9% by mass sodium hydroxide aqueous solution was added dropwise with ice cooling to accomplish 75 mol % neutralization. Then, 0.10 g (0.00037 mol) of potassium persulfate was added and dissolved therein, thereby preparing an aqueous monomer solution. The rotation speed of the stirrer was adjusted to 900 rpm. Then, the aqueous monomer solution was added into the separable flask, and the atmosphere within the system was sufficiently replaced with nitrogen. The flask was subsequently immersed in a water bath at 70° C., and polymerization reaction was carried out for one hour to obtain a polymerization slurry.

Next, after the rotation speed of the stirrer was changed to 1000 rpm, the flask was heated in an oil bath at 125° C. to distill 100 g of water out of the system while refluxing n-heptane into the system by azeotropic distillation of water and n-heptane. Then, 4.14 g (0.00048 mol) of a 2% by mass of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 90.7 g of a granular water-absorbent resin. The median particle diameter of the obtained water-absorbent resin was 340 μm.

Table 1 shows the results of evaluation of the water-absorbent resins produced in the examples and comparative examples, using the testing methods for evaluation described above, and Table 2 shows evaluation results of the absorbent articles.

TABLE 1

|  | Cavity area ratio (%) | Physiological saline-retention capacity (g/g) | Liquid flow rate index |
|---|---|---|---|
| Example 1 | 6 | 28 | 16 |
| Example 2 | 6 | 31 | 8 |
| Example 3 | 8 | 30 | 12 |
| Comparative Example 1 | 11 | 30 | 1 |
| Comparative Example 2 | 1 | 32 | 24 |
| Comparative Example 3 | 8 | 31 | 22 |
| Comparative Example 4 | 3 | 42 | 0 |
| Comparative Example 5 | 30 | 33 | 0 |

TABLE 2

|  | Liquid permeation time (sec) | | | | Liquid leakage |
|---|---|---|---|---|---|
|  | 1st time | 2nd time | 3rd time | Total |  |
| Example 1 | 29 | 18 | 21 | 68 | A (absence) |
| Example 2 | 26 | 16 | 18 | 60 | A |
| Example 3 | 27 | 18 | 20 | 65 | A |
| Comparative Example 1 | 35 | 23 | 29 | 87 | A |
| Comparative Example 2 | — | — | — | — | P (presence) |
| Comparative Example 3 | — | — | — | — | P |
| Comparative Example 4 | 34 | 27 | 31 | 92 | A |
| Comparative Example 5 | 42 | 57 | 82 | 181 | A |

In Table 2, for Comparative Examples 2 and 3, since the accurate liquid permeation time could not be measured due to liquid leakage of the absorbent article, it was expressed as "-".

As is clear from the results shown in Tables 1 and 2, the water-absorbent resins of Examples 1 to 3 in which the cavity area ratio is 2 to 10% and the liquid flow rate index is 5 to 20 exhibits excellent absorption performance and a high permeation rate with respect to liquids to be absorbed, and effectively reduces liquid leakages.

DESCRIPTION OF REFERENCE SIGNS

10: Sample stage
11: Water-absorbent resin
w: Particle length

The invention claimed is:

1. A water-absorbent resin comprising a polymer of a water-soluble ethylenically unsaturated monomer, wherein:
   the water-absorbent resin has a substantially spherical shape or a shape in which particles having a substantially spherical shape are aggregated,
   when a cross-sectional image of the water-absorbent resin obtained by X-ray computed tomography is observed, a ratio (cavity area ratio) as calculated by Equation (I) of an area of cavity portions in the cross-sectional image is 2 to 10%, and
   a liquid flow rate index as calculated by Equation (II) when a physiological saline liquid column flow rate test is performed on the water-absorbent resin having a particle diameter of 250 to 500 μm at 37° C. is 5 to 20:

(I) cavity area ratio [%]={total cross-sectional area (B) of cavity portions of the water-absorbent resin/(total cross-sectional area (A) of resin portions of the water-absorbent resin+total cross-sectional area (B) of cavity portions of the water-absorbent resin)}×100; and (II) liquid flow rate index={liquid flow rate (CPR2) during 10 second period between 50 seconds and 60 seconds after initiation of liquid flow/liquid flow rate (CPR1) during 10 second period after initiation of liquid flow}×100.

2. The water-absorbent resin according to claim 1, wherein the water-absorbent resin has a physiological saline-retention capacity of 35 g/g or less.

3. The water-absorbent resin according to claim 1, which is used in an adsorbent material designed to have a proportion of the water-absorbent resin of 50% by mass or more in the adsorbent material.

4. The water-absorbent resin according to claim 2, which is used in an adsorbent material designed to have a proportion of the water-absorbent resin of 50% by mass or more in the adsorbent material.

\* \* \* \* \*